US012290301B1

(12) United States Patent
Deukmedjian

(10) Patent No.: US 12,290,301 B1
(45) Date of Patent: May 6, 2025

(54) PERCUTANEOUS SURGICAL TREATMENT FOR PIRIFORMIS SYNDROME

(71) Applicant: Panacea Spine, LLC, Orlando, FL (US)

(72) Inventor: Ara Deukmedjian, Orlando, FL (US)

(73) Assignee: Panacea Spine, LLC, Orlando, FL (US)

( * ) Notice: Subject to any disclaimer, the term of this patent is extended or adjusted under 35 U.S.C. 154(b) by 0 days.

(21) Appl. No.: 18/809,260

(22) Filed: Aug. 19, 2024

(51) Int. Cl.
A61B 18/18 (2006.01)
A61B 18/08 (2006.01)
A61B 90/00 (2016.01)
A61B 18/00 (2006.01)

(52) U.S. Cl.
CPC ............ *A61B 18/082* (2013.01); *A61B 90/36* (2016.02); *A61B 2018/00315* (2013.01); *A61B 2018/00601* (2013.01); *A61B 2090/376* (2016.02)

(58) Field of Classification Search
CPC ..... A61B 17/02; A61B 90/06; A61B 17/0218; A61B 17/142; A61B 17/1604; A61B 17/1666; A61B 17/1746; A61B 17/1753; A61B 17/1796; A61B 17/56; A61B 17/848; A61B 17/8866; A61B 2017/0046; A61B 2017/0275; A61B 2017/561; A61B 2017/564; A61B 2090/062; A61B 2017/565; A61B 17/00234; A61B 2017/00022; A61B 2017/00026; A61B 2017/00119; A61B 2017/00128; A61B 2017/00725; A61B 2034/2048; A61B 2090/064; A61B 2090/065; A61B 2090/066; A61B 2560/0223; A61B 2562/0219; A61B 34/30; A61B 34/76; A61B 5/14551; A61B 5/14552; A61B 5/202; A61B 5/746
See application file for complete search history.

(56) References Cited

U.S. PATENT DOCUMENTS 7,105,028 B2 9/2006 Murphy
8,597,362 B2 12/2013 Shenoy et al.
9,078,672 B1 * 7/2015 Rosse ................ A61B 17/1631
(Continued)

OTHER PUBLICATIONS

Todd P. Pierce, M. D., Casey M. Pierce, M.D., Kimona Issa, M. D., Vincent K. McInerney, M. D., Anthony Festa, M.D., and Anthony J. Scillia, M.D.; "Arthroscopic Piriformis Release A Technique for Sciatic Nerve Decompression"; Arthoscopy Techniques; vol. 6, No. 1; (Feb. 2017); pp e163-e166 (Year: 2017).*
(Continued)

*Primary Examiner* — Michael F Peffley
*Assistant Examiner* — Amanda L Zink
(74) *Attorney, Agent, or Firm* — Gordon & Jacobson, P.C.

(57) ABSTRACT

A method is provided for treating chronic piriformis muscle inflammation, commonly referred to as piriformis syndrome. The method includes percutaneous advancing an electrocautery probe through an incision at the back of the buttock, and navigating the probe under medical imaging toward a proximal end of a femur bone adjacent the greater trochanter. The probe is activated to cut the piriformis muscle or piriformis muscle insertion tendon at or adjacent the greater trochanter of the proximal femur to free the muscle and permanently alleviate muscle pain and tenderness.

19 Claims, 4 Drawing Sheets

(56) References Cited

U.S. PATENT DOCUMENTS

| | | |
|---|---|---|
| 9,895,539 B1 | 2/2018 | Heit et al. |
| 10,478,317 B2 | 11/2019 | Chow |
| 11,420,052 B2 | 8/2022 | Doskocil et al. |
| 11,446,490 B2 | 9/2022 | Doskocil |
| 11,684,778 B2 | 6/2023 | Errico et al. |
| 11,730,519 B2 | 8/2023 | Shenoy et al. |
| 2002/0193797 A1* | 12/2002 | Johnson ............... A61F 2/4609 606/79 |
| 2003/0224019 A1 | 12/2003 | O'Brien |
| 2003/0229356 A1* | 12/2003 | Dye .................. A61F 2/4609 606/99 |
| 2004/0172038 A1* | 9/2004 | Dye .................. A61B 17/02 606/91 |
| 2004/0172039 A1* | 9/2004 | Dye .................. A61B 17/8875 606/99 |
| 2004/0236341 A1* | 11/2004 | Petersen ............. A61B 17/15 606/88 |
| 2005/0096748 A1* | 5/2005 | Yoon .................. A61B 17/56 623/22.4 |
| 2007/0259763 A1 | 11/2007 | McKeown et al. |
| 2008/0171065 A1 | 7/2008 | O'Brien |
| 2016/0250039 A1* | 9/2016 | Chow ............... B65D 81/3453 606/91 |
| 2021/0290215 A1 | 9/2021 | Amanatullah et al. |
| 2021/0383892 A1* | 12/2021 | Holzer ................. G16H 50/70 |
| 2022/0183857 A1* | 6/2022 | Siccardi ............. A61B 17/1659 |
| 2022/0233335 A1 | 7/2022 | Chow |

OTHER PUBLICATIONS

"Piriformis Syndrome Surgery", Jay Jagannathan, MD; Spine-health; Mar. 3, 2023.

"Posttraumatic Piriformis Syndrome: Diagnosis and Results of Operative Treatment"; Benson, Eric et al.; The Journal of Bone & Joint Surgery 81(7); p. 941, Jul. 1999.

"Surgical Treatment of Piriformis Syndrome"; Suk Ku Han, MD et al.; Clinics in Orthopedic Surgery, 2017; Jun.; 9(2); 136-144.

* cited by examiner

PERCUTANEOUS SURGICAL TREATMENT FOR PIRIFORMIS SYNDROME

BACKGROUND OF THE INVENTION

1. Field of the Invention

The present disclosure relates to treatments for pain. More particularly, the present disclosure is directed to a percutaneous image-guided treatment for piriformis muscle pain.

2. State of the Art

The piriformis muscle extends from the pelvic surface of the sacrum to the upper border of the greater trochanter of the femur. The piriformis muscle can be subject to tears and consequent inflammation. This inflammation results in lower back pain over the upper buttock and pain and extreme tenderness in the buttock. As a result of the proximity of the sciatic nerve to the inflamed piriformis muscle, the sciatic nerve can become irritated and result in weakness, a chronic nagging ache, tingling, numbness and/or pain that starts in the buttocks but can extend through the leg below the buttock; specifically along the course of the sciatic nerve, down the entire back of the femur and tibia, and in front of the tibia. This condition is quite common in the middle-aged and elderly populations.

Patients are frequently advised to stop running, bicycling, or performing any activity that elicits pain. Stretching exercises, although often recommended, are rarely beneficial treatments, and any movement that raises the knee forcibly will stretch the piriformis muscle and aggravate symptoms.

A common treatment is corticosteroid injection and local anesthetic into the site near where the piriformis muscle crosses the sciatic nerve. This may offer temporary relief. However, in many cases, the compression and pain return in time. In addition, injections often miss the muscle, or strike the sciatic nerve or the colon, and can lead to significant complications. Open MRI image guidance has permitted administering injections more reliably and accurately. However, the cost to access MRI equipment is high and access is not available at many facilities. In addition, the relief from corticosteroid injection may be temporary, requiring repeated treatment.

US Pub. No. 2008/0171065 to O'Brien has taught to deliver a therapeutically effective amount of botulinum toxin B ('Botox') into the piriformis muscle to cause muscle relaxation and pain relief. But again, the effects of local botulinum toxin B are temporary and require repeat treatment for many patients.

Open surgical treatments also have been performed. Such treatments surgically opening the patient with a 4 to 6 inch incision down through the gluteus maximus muscle, which is then retracted to obtain direct visual and surgical access to the piriformis muscle. However, the location of the open surgical approach can result in injury to the sciatic nerve, which runs close to the incision. Further, the approach is through an area of tissue that has a significant blood supply and also can result in significant bleeding during the surgery. Moreover, the significant incision, muscle manipulation, bleeding and potential for nerve disturbance can require significant time for healing.

SUMMARY OF THE INVENTION

A method is provided for treating piriformis muscle inflammation and the consequences thereof, such as of the type of a disorder commonly referred to as piriformis syndrome.

In an embodiment of the method, the method includes providing a rigid surgical probe having a distal tip, the distal tip of the surgical probe suitable for performing a percutaneous procedure. A small incision is created in the body of the patient at the back of the buttock. The distal tip of the surgical probe is advanced percutaneously through the incision and navigated under medical imaging toward a proximal end of a femur bone adjacent the greater trochanter. The surgical probe is activated to cut the piriformis muscle or piriformis muscle insertion tendon at or adjacent the greater trochanter of the proximal femur. Preferably, the muscle or tendon of the piriformis is cut between the lateral border of the sciatic nerve and the medial border of the greater trochanter. More preferably, the piriformis muscle is completely transected. This causes the piriformis muscle to be permanently freed from stretching between anchor points and the muscle pain is permanently alleviated. The piriformis muscle no longer can irritate the sciatic nerve, relieving all the potential consequences of pressing on the sciatic nerve.

In an embodiment of the method, the medical imaging is fluoroscopic imaging.

In an embodiment of the method, the surgical probe is an electrocautery probe.

In an embodiment of the method, the surgical probe is wanded in a plurality of directions at or adjacent the greater trochanter while activated in order to cut the piriformis muscle or its insertion tendon. In an embodiment of the method, the piriformis muscle and/or piriformis muscle insertion tendon are cauterized by the probe.

In an embodiment of the method, a medication is delivered to the piriformis muscle during the procedure. In an embodiment of the method, the medication is delivered prior to cutting the piriformis muscle and/or piriformis muscle insertion tendon. In an embodiment of the method, the medication is at least one of a local anesthetic and an anti-inflammatory medicine. In an embodiment of the method, the medication includes at least one of novocaine, bupivacaine, and methylprednisolone. Other medications can also be used. The medication is used to aid in any minor pain that could otherwise temporarily be experienced after the treatment; it is not intended to primarily manage the underlying inflammation of the piriformis muscle as prior treatments have relied upon. In an embodiment, the probe includes a lumen, and the medicine is delivered through the lumen of the probe.

The method provides a safe and effective procedure for percutaneous treatment of piriformis syndrome. The procedure is quick healing and provided permanent results.

DETAILED DESCRIPTION OF THE PREFERRED EMBODIMENTS

Figure 1:
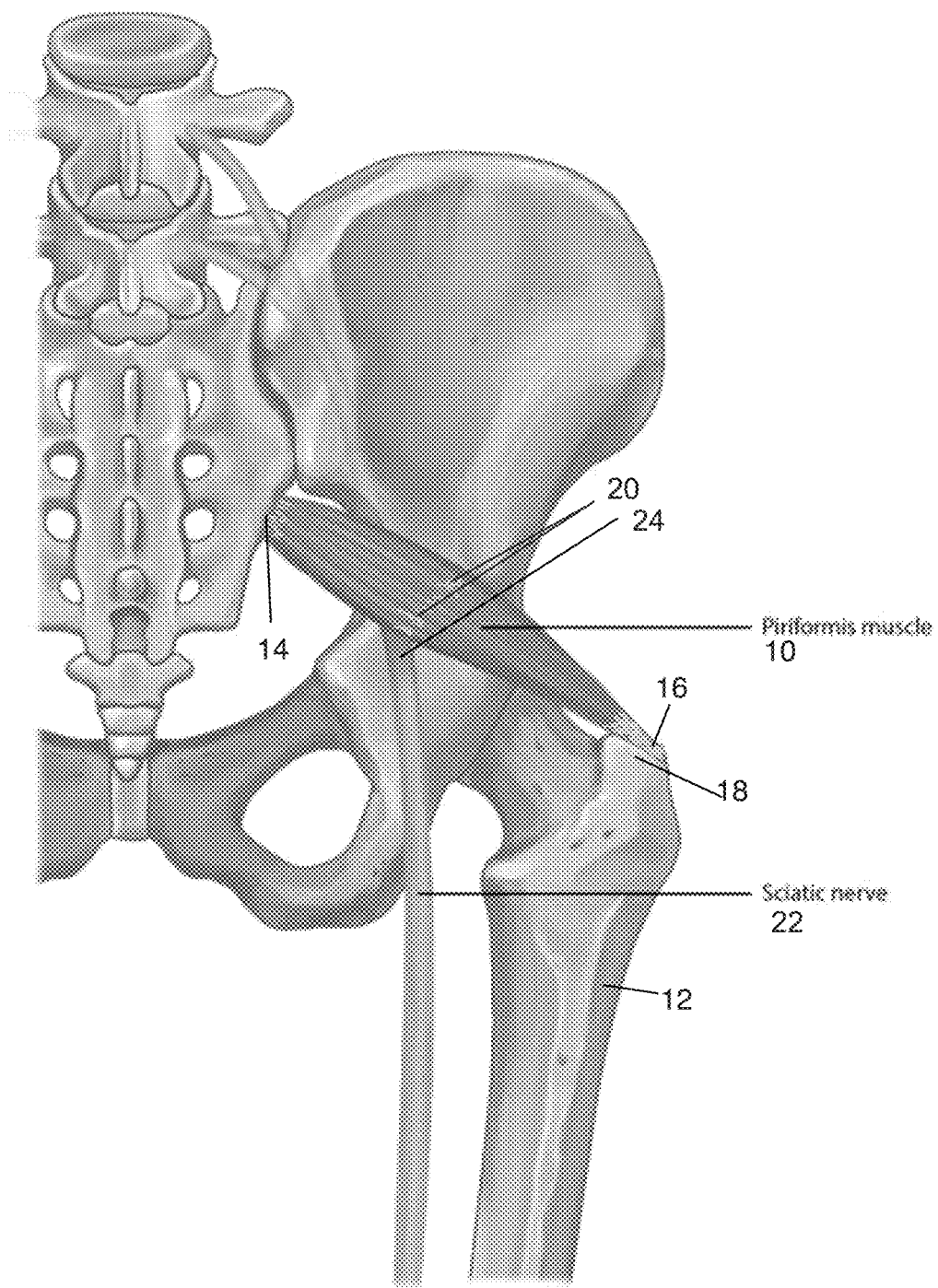
FIG. 1 is a view of select skeletal anatomy, a piriformis muscle extending between the greater trochanter of a femur and a sacrum, and a sciatic nerve impinged by the piriformis muscle.

Referring to FIG. 1, the piriformis muscle 10 extends between the femur 12 and sacrum 14. At the femoral side, a piriformis insertion tendon 16 extends from and attaches the piriformis muscle 10 to the greater trochanter 18 of the proximal femur 12. In certain individuals, the piriformis muscle 10 is chronically inflamed (e.g., as a result of tears 20), referred to as piriformis syndrome. The inflamed piriformis muscle 10 results in buttock pain, tenderness and swelling. In addition, as a result of the proximity and potential pressure from the inflamed piriformis muscle 10 on the sciatic nerve 22, the sciatic nerve may become irritated 24 and result in symptoms such as weakness, numbness and pain in the leg may result. A method is provided for treating piriformis syndrome.

Figure 2:
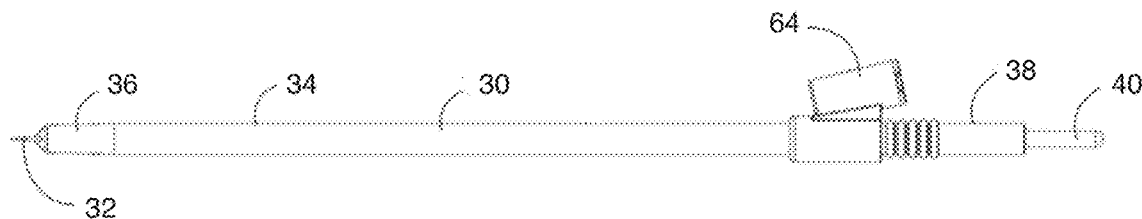
FIG. 2 is a side elevation of an embodiment of an electrocautery probe.
Figure 3:
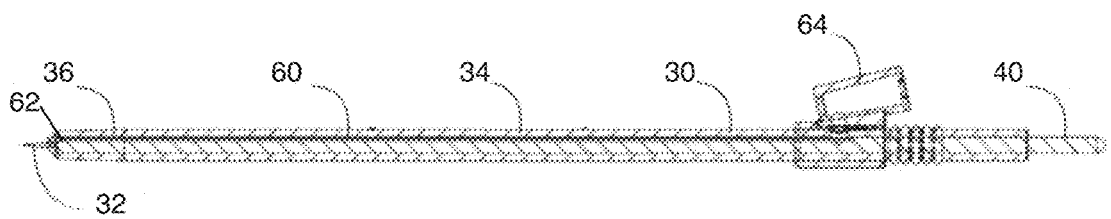
FIG. 3 is a longitudinal section view of the electrocautery probe of FIG. 2.
Figure 4:
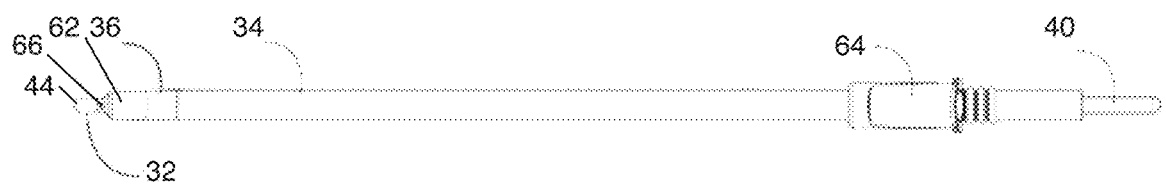
FIG. 4 is a top view of the electrocautery probe of FIG. 2.

In an embodiment of the method, the method includes providing a rigid surgical probe 30 having a distal tip 32, the distal tip of the surgical probe suitable for performing a percutaneous procedure. A preferred surgical probe 30 is an electrocautery probe. Turning to FIGS. 2, 3 and 4, one embodiment of an electrocautery probe is shown. The probe 30 includes rigid shaft 34, a metal distal tip 32 at a distal end 36 of the shaft that is adapted to cut when energized, and a proximal end 38. An electrode 40 extends through the shaft 34 into electrical communication with the distal tip 32 and also preferably protrudes from the proximal end 38. The shaft 34 includes an external insulated guard or barrier material 42 about the electrode 1216. The distal tip 32 preferably extends from a center of the distal end 36 of the shaft 34. The shaft 34 is preferably a unitary body from the proximal end 38 to the distal end 36. The shaft 34 preferably smoothly tapers to the distal end 36 without any interruption, protrusion, shoulder structure, or shrink wrap material than could catch on tissue; that is, it is preferred that the distal portion of the shaft have a smooth surface profile to aid in tissue insertion.

In an embodiment, the metal tip 32 has a length of 4.3 mm (0.17 inch), a thickness of 0.5 mm (0.02 inch) at where it extends from the shaft 34, and tapers over a distal 3.0 mm (0.12 inch) portion of its length; the tip has a width of 2.3 mm (0.09 inch), and has a radius of 1.14 mm (0.045 inch) forming a semicircular tapered distal edge 44. Each of the foregoing dimensions can also optimally be varied in a range of +20%. The distal tip 32 is sharp in a direction transverse to the radiused edge 44, and stiff, adapted to not bend under normal use.

Figure 5:
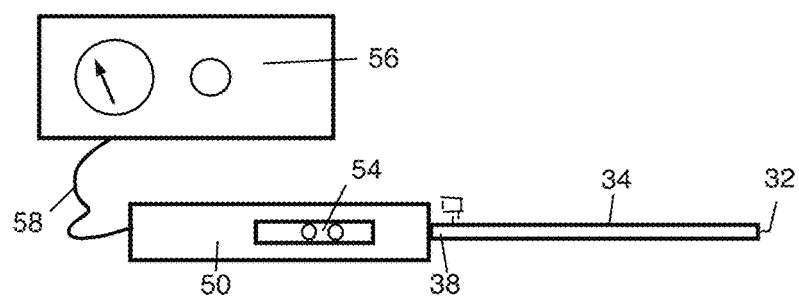
FIG. 5 is a schematic view of an electrocautery system used with the probe of FIG. 2.

Turning to FIG. 5, a handpiece or handle 50, preferably adapted to be removable from the shaft 34 at the electrode 40 (FIG. 4), is couplable at the proximal end 38 of the shaft 34. The handle 50 includes actuation controls 54 (e.g., to trigger one of coagulation or cutting RF energy to be applied from an RF generator 56 to the distal cutting tip 32) and electrical connection 58 to the RF generator 56. The shaft 34 is preferably a single use, disposable device, whereas the handle 50 may be reusable. Alternatively, the shaft 34 and handle 50 may be integrated together, or the actuation controls 54 may be operated by foot controller.

Referring to FIG. 3, a fluid lumen 60 extends through the shaft 34, preferably parallel to the electrode 40. The distal end 36 of the shaft 34 includes a tapered portion 62 that is adapted to interference fit within a female Luer connector to make a substantially fluid tight connection.

Referring to FIGS. 2 through 4, the proximal portion of the shaft 34 includes a syringe connector 64, preferably in the form of female Luer connector. The syringe connector 64 is in fluid communication with the lumen 60, which has an exit 66 at the tapered distal portion 62 of the shaft 34 adjacent the width-wise center of the distal cutting tip 32.

Figure 6:
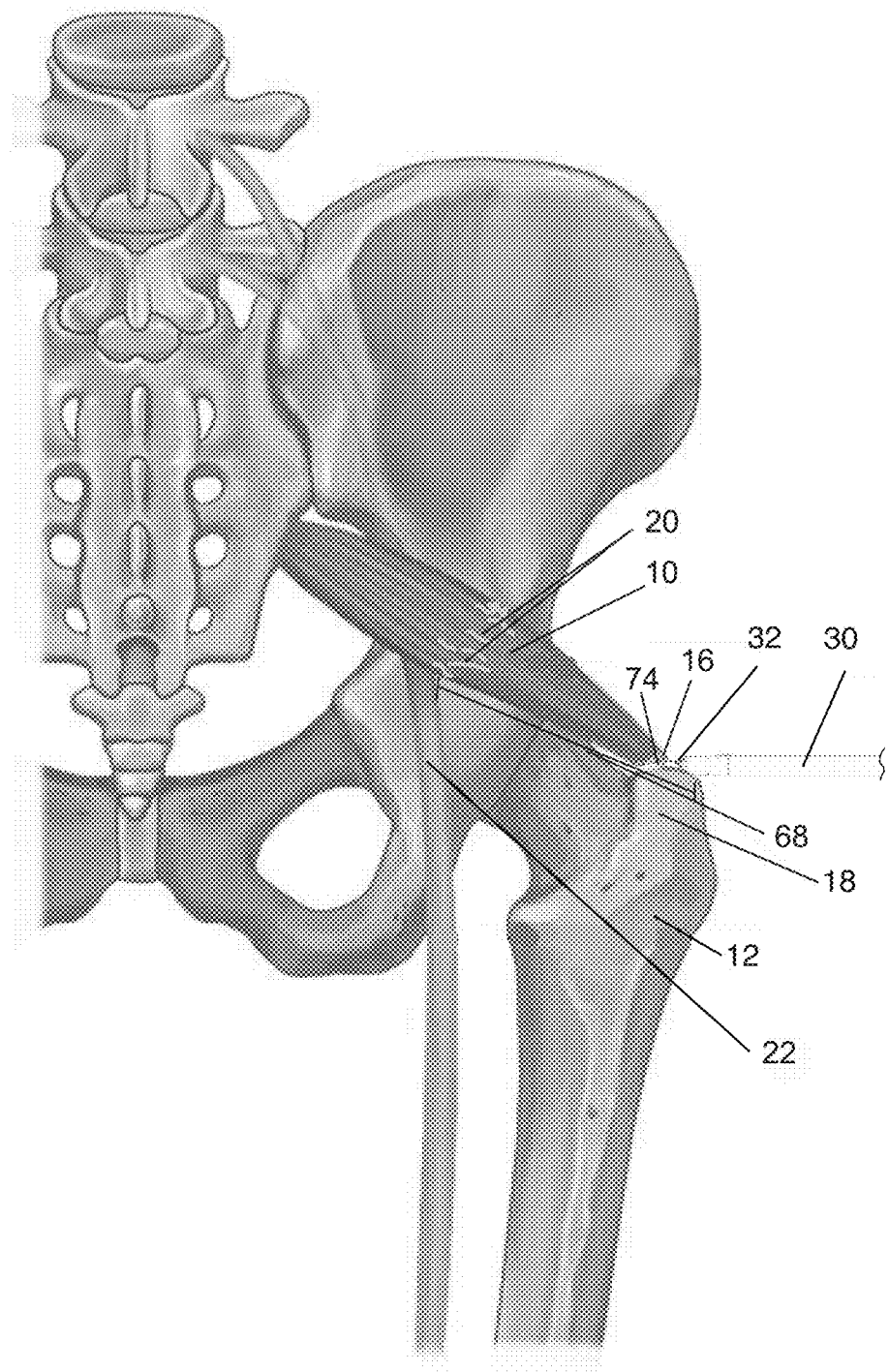
FIG. 6 illustrates a step in a method described herein.

Turning to FIG. 6, in a method of treatment, a small incision is created in the body of the patient at the back of the buttock. The incision is preferably smaller than 2 cm, and more preferably approximately 1 cm. The incision may be made with the surgical probe 30 or another surgical instrument, such as a scalpel. The distal tip 32 of the surgical probe 30 is advanced percutaneously through the incision and navigated under medical imaging toward a proximal end of a femur 10 adjacent the greater trochanter 18. The medical imaging is preferably fluoroscopy. The surgical probe 30 is activated to cut the piriformis muscle 10 or piriformis muscle insertion tendon 16. The piriformis muscle 10 or the piriformis muscle insertion tendon 16 is cut at a location 68 between a lateral border of a sciatic nerve 22 and a medial border of the greater trochanter 18. The piriformis muscle 10 or insertion tendon 16 is thereby released, preferably by complete transection, from the greater trochanter 18. Preferably, the piriformis muscle 10 or insertion tendon 16 is cut at or adjacent the greater trochanter 18 of the proximal femur 12.

Figure 7:
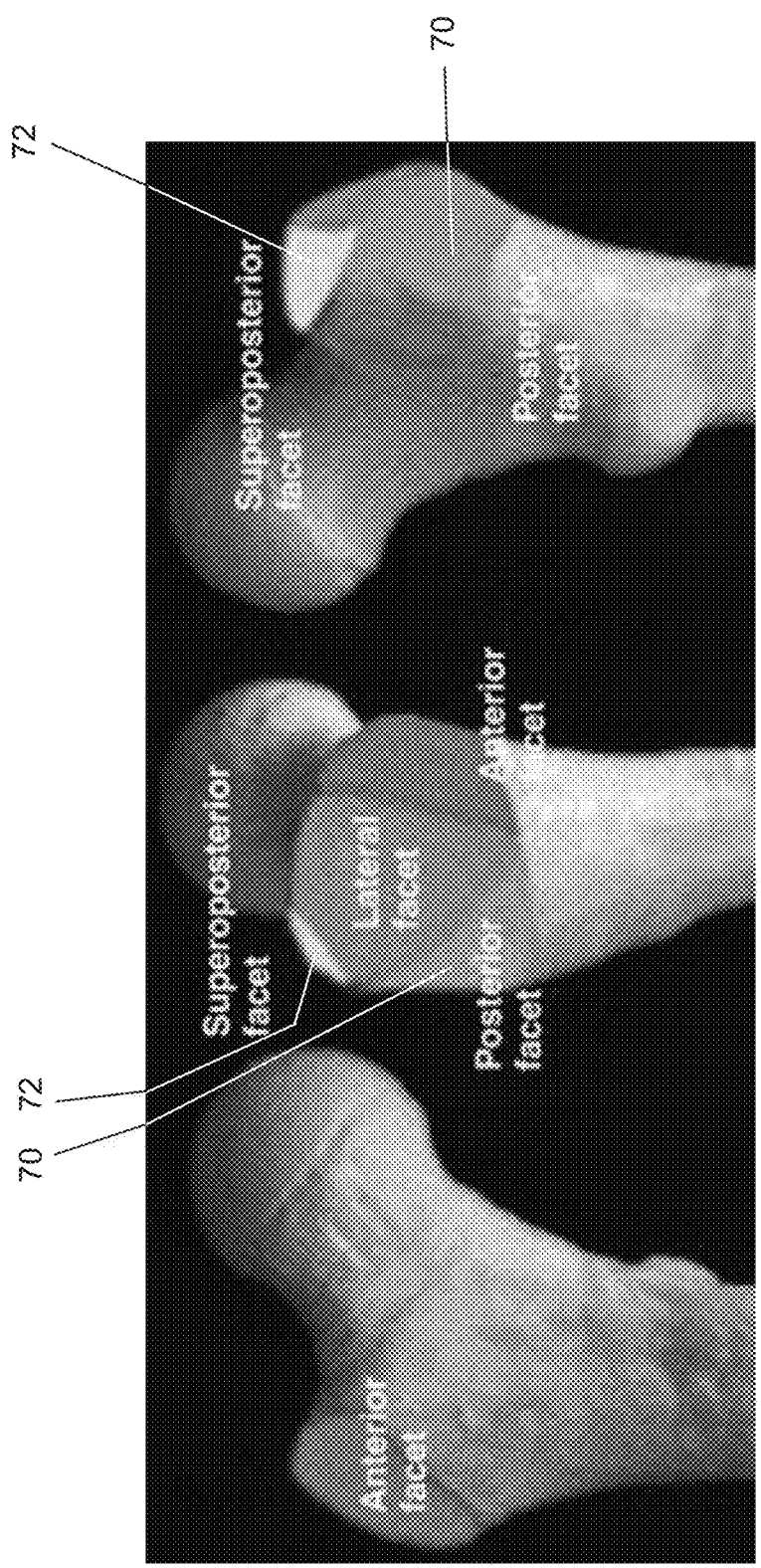
FIG. 7 illustrates preferred aspects of the method described herein.

In an embodiment of the method, the surgical probe 30 is wanded in a plurality of directions over a surface area of the greater trochanter 18, and preferably along three axes of movement over and above the greater trochanter while activated in order to cut the piriformis muscle 10 or its insertion tendon 16. Referring to FIGS. 6 and 7, in an exemplar embodiment of the method, the cutting tip 32 of the probe is wanded across the medial and posterior sides of the posterior facet 70 and the superoposterior facet 72 of the greater trochanter 18, the facets at which the insertion tendon 16 (FIG. 1) for the piriformis muscle 10 is attached to the greater trochanter 18. The insertion tendon 16 can be removed directly from the bone at these facets 70, 72, the insertion tendon 16 can be cut slightly off/above the surface of the bone over these facets 70, 72, and/or the piriformis muscle 10 can be cut as it extends from the insertion tendon 16. All cutting 74 (FIG. 6) is preferably a complete transection through the tissue so that the piriformis muscle 10 is no longer connected to the greater trochanter 18 in any meaningful manner that permits both contraction and stretching of the muscle or which allows the sciatic nerve 22 to be irritated by the piriformis muscle. All cutting is preferably within 10 centimeters of the greater trochanter, may be within 5 centimeters of the greater trochanter 18, may be within 3 centimeters, or may be within 1 centimeter of the greater trochanter. With the preferred electrocautery probe, the piriformis muscle and/or piriformis muscle insertion tendon are cauterized by the probe. As a result of the procedure, the piriformis muscle 10 is freed from its position and released of compression of the sciatic nerve 22, thereby permanently alleviating pain.

An aspect of the method is that the surgeon does not directly visualize the piriformis muscle while releasing the piriformis muscle from its attachment to the greater trochanter; all visualization is indirect via medical imaging. Further, the preferred medical imaging principally provides visualization of the bones and instruments which are used as guideposts; the surgeon then further relies upon the feel of the instruments against the bone and muscle in conjunction with the visualization to determine the location and completion of the release of the piriformis muscle from the greater trochanter.

This approach is safe, as the area of the transection and cauterization are in the vicinity of no major nerves or arteries. Further, if the tendon is transected, the tendon is avascular and should not result in any significant bleeding. Any bleeding at the muscle can be resolved via the cauterization.

In an embodiment of the method, a medication is delivered to the piriformis muscle 10 during the procedure. The medication may be delivered through the probe; i.e., from the syringe connector 64 through the fluid lumen 60 and out exit 66 at the tapered distal portion 62 of the shaft 34 adjacent the cutting tip 32. Alternatively, particularly where a probe is used that does not include a fluid lumen, the medication may be delivered via a separate syringe injection. The medication may be delivered prior to cutting the piriformis muscle and/or piriformis muscle insertion tendon. In an embodiment of the method, the medication is at least one of a local anesthetic and an anti-inflammatory medicine. In an embodiment of the method, the medication includes at least one of novocaine, bupivacaine, and methylprednisolone. Other medications can also be used. The medication is used to aid in any minor pain that could otherwise temporarily be experienced after the treatment. In an embodiment, the probe includes a lumen, and the medicine is delivered through the lumen of the probe.

The method provides a safe and effective procedure for percutaneous treatment of piriformis syndrome. The procedure is quick healing and provided permanent results.

There have been described and illustrated herein embodiments of methods for treating piriformis syndrome. While embodiments of the method have been described, it is not intended that the invention be limited thereto, as it is intended that the invention be as broad in scope as the art will allow and that the specification be read likewise. Therefore, while an electrocautery probe is described as the preferred instrument for cutting the piriformis muscle or insertion tendon, other device can similarly be used to cut the target tissue. By way of example, and not be limitation, a laser probe, a mechanically abrasive probe, chemical delivery probe, a cryogenic cooling probe, an ultrasonic energy delivery probe, a microwave energy probe, or other energy or stimulation delivery probe activatable for transecting the target tissue can similarly be used. It will therefore be appreciated by those skilled in the art that yet other modifications could be made to the provided invention without deviating from its scope as claimed.

What is claimed is:

1. A method of treating piriformis syndrome of a human patient, in which the piriformis muscle extends from the sacrum to a greater trochanter of a proximal femur, comprising:
   a) making an incision in the buttock of the patient;
   b) percutaneously advancing a treatment probe through the incision to at or adjacent the upper trochanter of the proximal femur;
   c) without inserting any medical visualization system into the patient, using the treatment probe to release the piriformis muscle from the greater trochanter by cutting at least one of the piriformis muscle and a piriformis muscle insertion tendon at a location between a lateral border of a sciatic nerve and a medial border of the greater trochanter; and
   d) removing the treatment probe from the incision.

2. The method of claim 1, wherein the treatment probe is an electrocautery probe.

3. The method of claim 1, wherein the method is performed under fluoroscopic medical imaging.

4. The method of claim 1, wherein the releasing the piriformis muscle includes transecting one of the piriformis muscle and the piriformis muscle insertion tendon.

5. The method of claim 4, wherein the transecting is located within 10 cm of the greater trochanter.

6. The method of claim 4, wherein the transecting is located within 5 cm of the greater trochanter.

7. The method of claim 4, wherein the transecting is located within 3 cm of the greater trochanter.

8. The method of claim 4, wherein the transecting is located within 1 cm of the greater trochanter.

9. The method of claim 1, wherein the releasing includes wanding the treatment probe over the surface of the greater trochanter to release attachment of the piriformis muscle relative to the greater trochanter.

10. The method of claim 1, wherein the releasing includes separating the piriformis muscle from the posterior facet and the superoposterior facet of the greater trochanter.

11. The method of claim 1, further comprising delivering medication to the piriformis muscle.

12. The method of claim 11, wherein the medication is delivered prior to the release of the piriformis muscle.

13. The method of claim 12, wherein the treatment probe includes a fluid lumen, and the medication is delivered through the fluid lumen.

14. A method of treating piriformis syndrome of a human patient, in which the piriformis muscle extends from the sacrum to a greater trochanter of a proximal femur, comprising:
   making an incision in a buttock of the human patient;
   delivering medication to the piriformis muscle; and
   without inserting any medical visualization system into the patient, percutaneously surgically releasing the piriformis muscle from the greater trochanter by advancing a rigid electrocautery probe through the incision, and moving the electrocautery probe within the incision to perform a transection of tissue that is a portion of or attached to the piriformis muscle and which is located between a lateral border of a sciatic nerve and a medial border of the greater trochanter.

15. A method of treating piriformis syndrome of a human patient, in which the piriformis muscle extends from the sacrum to a greater trochanter of a proximal femur, comprising:
   a) delivering medication to the piriformis muscle; and
   b) percutaneously surgically releasing the piriformis muscle from the greater trochanter by transecting at least one of the piriformis muscle and a piriformis muscle insertion tendon at a location between a lateral border of a sciatic nerve and a medial border of the greater trochanter, all without inserting any medical visualization system into the patient.

16. The method of claim 15, wherein the location is within 10 cm of the greater trochanter.

17. The method of claim 15, wherein the location is within 3 cm of the greater trochanter.

18. The method of claim 15, wherein the location is within 1 cm of the greater trochanter.

19. The method of claim 14, wherein the method is performed under fluoroscopic imaging.

* * * * *